US005714499A

United States Patent [19]

Semple et al.

[11] Patent Number: 5,714,499

[45] Date of Patent: Feb. 3, 1998

[54] 3-AMINO-2-OXO-1-PIPERIDINEACETIC DERIVATIVES CONTAINING AN ARGININE MIMIC AS ENZYME INHIBITORS

[75] Inventors: Joseph E. Semple; Odile E. Levy; Ruth F. Nutt; William C. Ripka, all of San Diego, Calif.

[73] Assignee: Corvas International, Inc., San Diego, Calif.

[21] Appl. No.: 261,498

[22] Filed: Jun. 17, 1994

[51] Int. Cl.$^6$ ........................ A61K 31/445; C07D 401/12

[52] U.S. Cl. .................... 514/316; 514/222.5; 514/237.2; 514/237.8; 514/252; 514/255; 514/256; 514/326; 514/369; 514/425; 544/8; 544/129; 544/162; 544/309; 544/310; 546/208; 546/209; 548/184; 548/185; 548/544

[58] Field of Search ................................. 514/316, 222.5, 514/237.2, 237.8, 252, 255, 256, 326, 369, 425; 546/190, 208, 209; 544/8, 129, 162, 309, 310; 548/184, 185, 544

[56] References Cited

FOREIGN PATENT DOCUMENTS

| | | |
|---|---|---|
| 0 526 877 A2 | 8/1993 | European Pat. Off. . |
| 2 490 632 | 9/1981 | France . |

OTHER PUBLICATIONS

Skiles, J.W. et al, Biorg. Med. Chem. Lett. 1993, 3(4), pp. 773–778.

R. Freidinger, et al., "Protected Lactam–Bridged Dipeptides for Use as Conformational Constraints in Peptides," *J. Org. Chem.*, 47:104–109, 1982.

H. Vieweg, et al., "Synthese von N–alpha–(arylsulphonylglycyl)–3–amidinophenulalaninest ern als aktive and relativ spezfische Inhibtoren von Faktor Xa," *Pharmazie*, vol. 42, No. 4, Apr. 1987, Berlin DD p. 268.

G. Wagner, et al., "Synthese von N–alpha–(Tosyl–beta–alanyl)–und N–alpha–(Tosyl–espsilon–aminocapronyl) amidinophenylalanylamiden als stark wirksame thrombininhititoren,"*Pharmazie*, vol. 39, No. 5, May 1984, Berlin DD pp. 315–317.

D. Carini, et al., "Nonpeptide Angiotensin II Receptor Antagoists:The Discovery of a Series of V–(Biphenylylmethyl) imidazoles as Potent, Orally Active Antihypertensives," *J. Med. Chem.*, vol. 34, No. 8, pp. 2525–2547, 1991.

*Primary Examiner*—C. Warren Ivy
*Assistant Examiner*—Garth M. Dahlen
*Attorney, Agent, or Firm*—Lyon & Lyon LLP

[57] ABSTRACT

The present invention discloses peptide aldehydes which are potent and specific inhibitors of thrombin, their pharmaceutically acceptable salts, pharmaceutically acceptable compositions thereof, and methods of using them as therapeutic agents for disease states in mammals characterized by abnormal thrombosis.

32 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 5 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 1:

```
Gly Gly Val Arg Gly
1               5
```

( 2 ) INFORMATION FOR SEQ ID NO: 2:

( i ) SEQUENCE CHARACTERISTICS:
( A ) LENGTH: 5 AMINO ACIDS
( B ) TYPE: AMINO ACID
( D ) TOPOLOGY: LINEAR ( i i ) MOLECULE TYPE: PEPTIDE ( i x ) FEATURE:
( D ) OTHER INFORMATION:

( x i ) SEQUENCE DESCRIPTION: SEQ ID NO: 2:

```
Phe Ser Ala Arg Gly
1               5
```

3-AMINO-2-OXO-1-PIPERIDINEACETIC DERIVATIVES CONTAINING AN ARGININE MIMIC AS ENZYME INHIBITORS

TECHNICAL FIELD

In one aspect, the present invention relates compounds which are potent and specific inhibitors of thrombin. In another aspect, the present invention relates to novel peptide aldehydes, their pharmaceutically acceptable salts, and pharmaceutically acceptable compositions thereof which are useful as potent and specific inhibitors of blood coagulation in vitro and in vivo in mammals. In yet another aspect, the invention relates to methods of using these inhibitors as therapeutic agents for disease states in mammals characterized by abnormal thrombosis.

BACKGROUND

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation.

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic Mechanisms", Disorders of Hemostasis, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", Blood, 76: 1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. Invest., 71: 1383–1391(1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105: 58 (1964). Beyond its direct role in the formation and stabilization of fibrin rich clots, the enzyme has been reported to have profound bioregulatory effects on a number of cellular components within the vasculature and blood. Shuman, M. A., Ann. NY Acad. Sci., 405: 349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84: 18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., Platelets in Biology and Pathology, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., Blood, 77: 2641 (1991). This positive feedback process results in the local generation of large concentrations of thrombin within the vicinity of the thrombus which supports further thrombus growth and extension. Mann, K. G. et al., Blood, 76: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., Biochemistry, 27: 769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., Science, 235: 1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. USA, 72: 131 (1975). The direct interaction of thrombin with vascular smooth muscle also results in vasoconstriction. Walz, D. A. et al., Proc. Soc. Expl. Biol. Med., 180: 518 (1985). Thrombin acts as a direct secretagogue inducing the release of a number of bioactive substances from vascular endothelial cells including tissue plasminogen activator. Levin, E. G. et al., Thromb. Haemost., 56: 115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet a-granules following thrombin-induced activation. Ross, R., N. Engl. J. Med., 314: 408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W.B. Saunders Co. (Fuster, V. and Verstraete, M. edit. 1991); Califf, R. M. and Wilierson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., J. Am. Coil. Cardiol., 67: 3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., J. Am. Coil. Cardiol., 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

P4 P3 P2 P1 P1'

Gly-Gly-Val-Arg/Gly Fibrinogen Aα Chain

Phe-Ser-Ala-Arg/Gly Fibrinogen Bβ Chain

Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolylboroarginine (Ac-(D-Phe)-Pro-boroArg) have been reported to inhibit thrombin by directly binding to the active site of the enzyme. Bajusz, S., Symposia Biologica Hungarica, 25: 277 (1984), Bajusz, S. et al, J. Med. Chem., 33: 1729 (1990) and Bajusz, S. et al., Int. J. Peptide Protein Res. 12: 217 (1970); Kettner, C. and Shaw, E., Methods Enzymol., 80: 826 (1987), Kettner, C. et al., EP 293,881 (published Dec. 7, 1988), Kettner, C., et al., J. Biol. Chem., 265: 18209 (1990). These molecules have been reported to be potent anticoagulants in the prevention of platelet-rich arterial thrombosis. Kelly, A. B. et al., Thromb. Haemostas., 65: 736 at abstract 257 (1991). Other peptidyl aldehydes have been proposed or reported as inhibitors of thrombin. Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which differ in structure from those containing a uncharged amino acid in the P3 recognition subsite have been reported.

The compound, Argatroban (also called 2R,4R-4-methyl-1-[N-2-(3-methyl-1,2,3,4-tetrahydro-8-quinolinesulfonyl)-

L-argininal]-2-piperdinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101: 440 (1981). Argatroban has been reported to be a potent antithrombotic agent in several experimental models of acute arterial thrombosis. Jang, I. K. et al., in both Circulation, 81: 219 (1990) and Circ. Res., 67: 1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., Thromb. Haemostas., 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., Thromb. Haemostas., 64: 344 (1990). It has been reported to inhibit thrombin by binding to both its anion-binding exo-site and to its catalytic active site which are distinct and physically distant from each other. Rydel, T. J. et al., Science, 249:277 (1990). Hirudin has been reported to be a potent antithrombotic agent in vivo. Markwardt, F. et al., Pharmazie, 43: 202 (1988); Kelly, A. B. et al., Blood, 77:1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., Circulation, 84: 232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264: 8692 (1989); Naski, M. C. et al., J. Biol. Chem., 265: 13484 (1990). The region of hirudin represented by hirugen has been reported, as according to by x-ray crystallographic analysis, to bind directly to the exo site of thrombin. Skrzypczak-Jankun, E. et al., Thromb. Haemostas., 65: 830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, L. W. et al., J. Biol. Chem, 266:16977 (1991). Hirugen also is reported to block thrombin-mediated platelet aggregation. Jakubowski, J. A. and Maraganore, J. M., Blood, 75: 399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., Biochemistry, 29: 7095 (1990). The hirulogs have been reported to be an effective antithrombotic agents in preventing both fibrin-rich and platelet-rich thrombosis. Maraganone, J. M. et al., Thromb. Haemostas., 65: 651 at abstract 17 (1991).

Certain benzamidines have been reported to inhibit thrombin though non-selectively. 4-amidinophenylpyruvic acid (APPA) has been reported to be a thrombin inhibitor with low toxicity and favourable pharmacokinetics. However, this compound was reported to be non-selective, inhibiting trypsin, plasmin and kallikrein. Markwardt et al., Thromb. Res., 1:243–52 (1972). Other benzamidine-derived structures which have been reported to inhibit thrombin include the cylic amides of $N^{\alpha}$-substituted 4-amidinophenylalanine and 2-amino-5-(4-amidinophenyl)-1-valeric acid. The inhibitory constant displayed by these compounds was reported to be in the micromolar range. Markwardt et al., Thromb. Res., 17:425–31 (1980). Moreover, derivatives of 4-amidinophenylalanine whose α-amino group is linked to the arylsulfonyl residue via an ω-aminoalkylcarboxylic acid as spacer have also been assessed for their inhibitory effect. Among these $N^{\alpha}$-(2-naphthylsulphonylglycyl) -4-amidino-phenylalanine piperidide (α-NAPAP) has been reported to possess an affinity for thrombin ($K_i$=6×$10^{-9}$M). Banner et al., J. Biol. Chem., 266:20085 (1991) and Sturzebecher et al., Thromb. Res., 29:635–42 (1983).

Certain bis-benzamidines have been reported to inhibit thrombin. The antithrombin activity of bis-benzamidines was reported to increase with the length and bulkiness of the central chain. However, these compounds were reported to be generally toxic in the micromolar range where they are also inhibitory. Geratz et. al., Thromb. Diath. Haemorrh., 29:154–67 (1973); Geratz et. al., J. Med. Chem., 16:970–5 (1973); Geratz et. al., J. Med. Chem., 19:634–9 (1976); Walsmann et. al., Acta Biol. Med. Germ., 35:K1–8 (1976); and Hauptmann et. al., Acta Biol. Med. Germ., 35:635–44 (1976).

Certain amidino-bearing aromatic ring structures such a beta-naphthamidines have been reported to possess modest antithrombin and anticoagulant activity. This class of compounds include the non-selective 6-amidino-2-naphthyl-4-guanidinobenzoate dimethanesulfonate (FUT 175). Fuji et al., Biochem. Biophys. Acta, 661:342–5 (1981); and Hitomi et. al., Haemostasis, 15:164–8 (1985).

Certain phenylguanidines have been reported to inhibit thrombin. Derivatives of 4-guanidinophenylalanine with inhibitory constants in the micromolar range have been reported to inhibit thrombin. This class includes the $N^{\alpha}$-tosylated and dansylated 4-guanidino phenylalanine piperidides. Claeson et. al., Thromb. Haemostas., 50:53 (1983). Another compound, [Ethyl p-(6-guanidinohexanoyloxy) benzoate] methane sulfonate (FOY) was reported to be a non-selective competitive inhibitor of thrombin. Ohno et al., Thromb. Res., 19:579–588 (1980).

SUMMARY OF THE INVENTION

The present invention is directed to novel peptide aldehyde compounds having an arginine mimic at $P_1$ and a lactam grup as part of the peptide backbone. These compounds are active as selective inhibitors of thrombin.

Novel compounds of the present invention have the following formula:

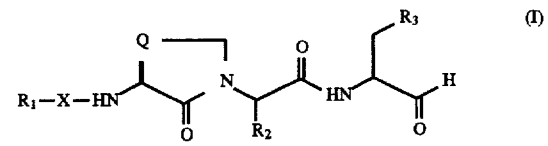

wherein:

(a) X is selected from the group consisting of —S(O)$_2$—, —NH—S(O)$_2$—, N(R')—S(O)$_2$—, —C(=O)—, —OC(=O)—, and —NH—C(=O)— wherein R' is alkyl of 1 to about 4 carbon atoms, aryl of about 6 to about 14 carbon atoms or aralkyl of about 6 to about 15 carbon atoms;

(b) $R_1$ is selected from the group consisting of:

(1) alkyl of about 3 to about 10 carbon atoms, (2) alkyl of 1 to about 3 carbon atoms substituted with cyclic alkyl of about 5 to about 8 carbon atoms, (3) alkenyl of about 3 to about 6 carbon atoms which is optionally substituted with cyclic alkyl of about 5 to about 8 carbon atoms, (4) aryl of about 6 to about 14 carbon atoms which is optionally mono-substituted with $Y_1$ and $Y_2$, (5) aralkyl of about 6 to about 15 carbon atoms which is optionally mono-substituted in the aryl ring with $Y_1$ or optionally di-substituted in the aryl ring with $Y_1$ and $Y_2$, (6) aralkenyl of about 8 to about 15 carbon atoms which is optionally mono-substituted in the aryl ring with $Y_1$ or optionally di-substituted in the aryl ring with $Y_1$ and $Y_2$,

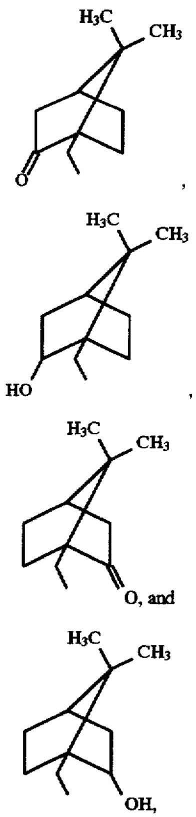

where $Y_1$ and $Y_2$ are independently selected from halogen, cyano, nitro, —COOH, —C(O)OZ$_1$, —Z$_1$, —OZ$_1$, —OH, —P(O)$_3$H, tetrazolyl, —S(O)3$_H$ and —S(O)$_m$Z$_1$ wherein m is 0, 1 or 2 and $Z_1$ is alkyl of 1 to about 12 carbon atoms, aryl of about 6 to about 14 carbon atoms and aralkyl of about 6 to about 15 carbon atoms;

(c) Q is selected from the group consisting of —CH$_2$—, —(CH$_2$)$_2$—, and —CH$_2$S(O)$_n$— where n is 0, 1 or 2;

(d) $R_2$ is selected from the group consisting of hydrogen, alkyl of 1 to 4 carbon atoms or alkenyl of 2 to 4 carbon atoms; and (e) $R_3$ is selected from the group consisting

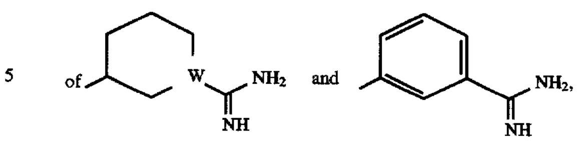

where W is nitrogen or carbon; and pharmaceutically acceptable salts thereof.

Among other factors, the present invention is based on our finding that the compounds of our invention are active as potent and selective inhibitors of thrombin. In particular, certain preferred compounds are active as very potent inhibitors of thrombin, yet are significantly less active (on the order of several orders of magnitude) as inhibitors of plasmin and trypsin. This selectivity for inhibition of thrombin gives these compounds a therapeutic advantage in treating or preventing thrombosis in a mammal suspected of having a condition characterized by abnormal thrombosis.

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound the present invention or pharmaceutical composition comprising such a compound.

Definitions

In accordance with the present invention and as used herein, the following terms are defined to have following meanings, unless explicitly stated otherwise.

The term "alkyl" refers to saturated aliphatic groups including straight-chain, branched-chain and cyclic groups.

The term "alkoxy" refers to a group having the formula, R—O—, wherein R is an alkyl group.

The term "aryl" refers to aromatic groups which have at least one ring having a conjugated pi electron system and includes carbocyclic aryl, heterocyclic aryl and biaryl groups, all of which may be optionally substituted.

The term "aryloxy" refers to a group having the formula, R—O—, wherein R is an aryl group.

The term "aralkyl" refers to an alkyl group substituted with an aryl group. Suitable aralkyl groups include benzyl, picolyl, and the like, all of which may be optionally substituted.

The term "aralkoxy" refers to a group having the formula, R—O—, wherein R is an aralkyl group.

The term "amino acid" refers to both natural, unnatural amino acids, in their D and L stereoisomers if their structure allow such stereoisomeric forms, and their analogs. Natural amino acids include alanine (Ala), arginine (Arg), asparagine (Ash), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Set), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid residue" refers to radicals having the structure: (1) —C(O)—R—NH—, wherein R typically is —CH(R')-, wherein R' is H or a carbon containing substituent; or (2)

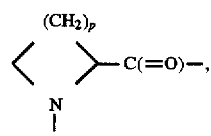

wherein p is 1, 2 or 3 representing the azetidinecarboxylic acid, proline or pipecolic acid residues, respectively.

The term "Ala(3-guanPip)-al" refers to the residue of 3-[3-piperidyl-(N-guanidino)]-alaninal the residue which has the formula:

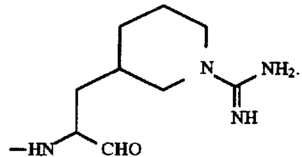

The term "Ala(3-guanPip)-ol" refers to the residue of 3-[3-piperidyl-(N-guanidino)]-alaninol the residue which has the formula:

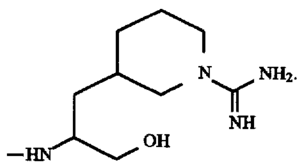

The term "homoAla(cyclo)-Gly" refers to the residue of (S)-3-amino-2-oxo-1-pyrrolidinacetic acid which has the formula:

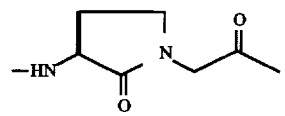

The term "norVal(cyclo)-Gly" refers to the residue of (S)-3-amino-2-oxo-1-piperidineacetic acid which has the formula:

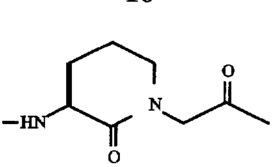

In addition, the following abbreviations stand for the following:

"N-alpha-t-butoxycarbonyl-$N^g$-nitro-L-arginine" refers to the compound which has the formula:

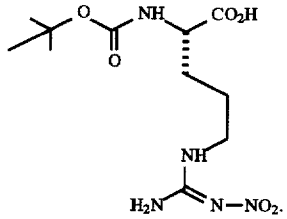

"(S)-Ng-nitroargininol hydrochloride" refers to the compound which has the formula:

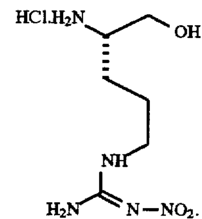

"Boc" refers to t-butoxycarbonyl.

"BOP" refers to benzotriazol-1-yl-oxy-tris-(dimethylamino) -phosphonium hexafluorophosphate.

"Brine" refers to an aqueous saturated solution of sodium chloride.

"$BzlSO_2$—" refers to benzylsulfonyl.

"EDC" refers to 1-ethyl-3-(3-dimethylamino-propyl) carbodiimide hydrochloride salt.

"HCl " refers to hydrochloric acid.

"HBTU" refers to 2-(1H-benzotriazol-1-yl)-1,1,3,3-tetramethyluronium hexafluorophosphate.

"HOBt" refers to 1-hydroxybenzotriazole monohydrate.

"2-PrPen" refers to 2-propylpentanoyl.

"$LiAlH_4$" refers to lithium aluminum hydride.

"$LiAlH_2(OEt)_2$ refers to lithium aluminum dihydride diethoxide.

"TBTU" refers to 2-(1H-benzotriazol-1-yl)-1,1,3,3-tetramethyluronium tetrafluoroborate.

DETAILED DESCRIPTION OF THE INVENTION

Preferred Compounds

Figure 1:
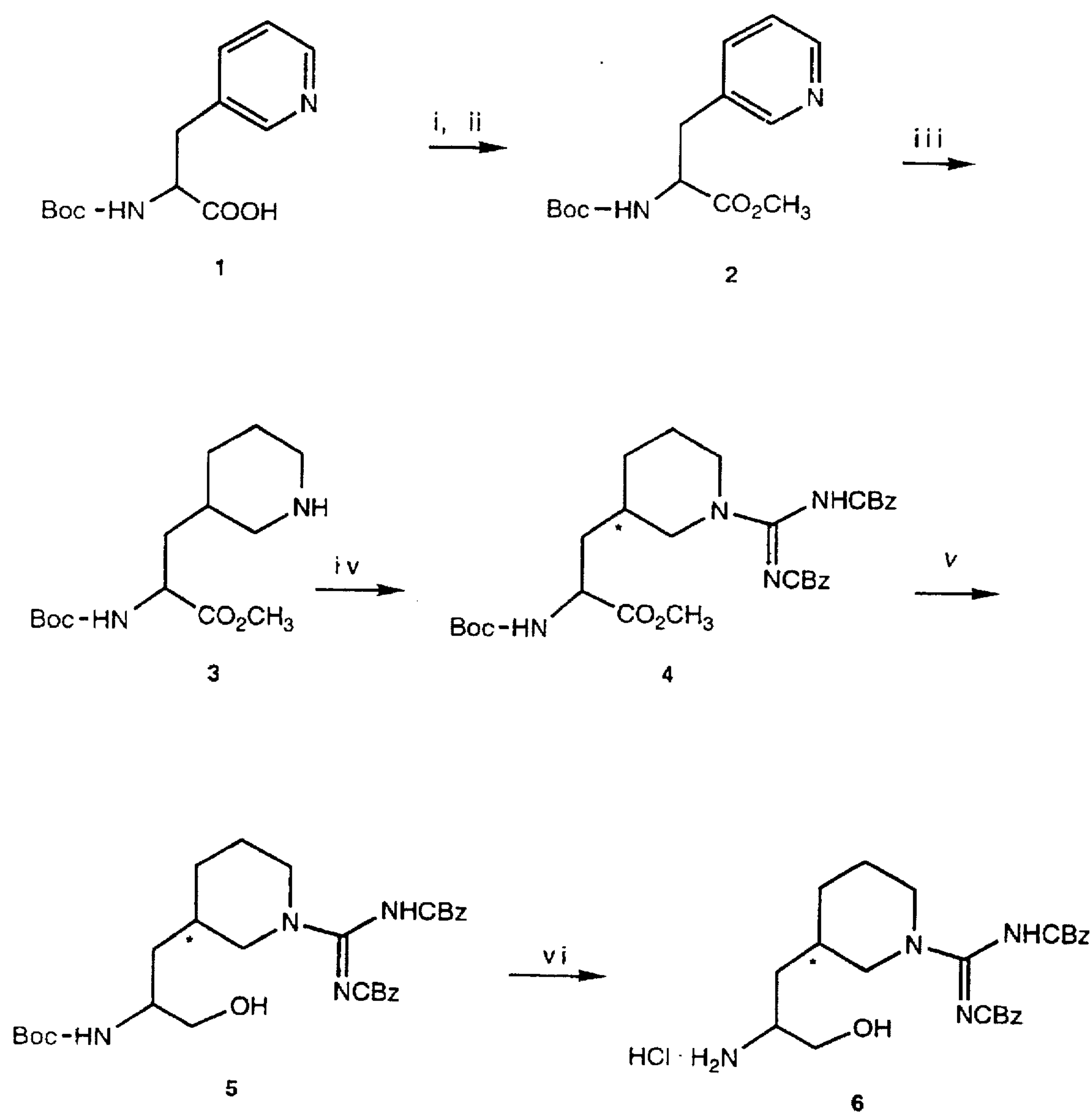
FIG. 1 depicts the reaction scheme for preparation of an intermediate used for the synthesis of the compounds of the present invention. In this figure, "i" through "vi" are defined as: i) thionyl chloride, methanol; ii) di-tert-butyl dicarbonate, pH 7–8; iii) hydrogen gas, platinum oxide in ethanol, water and acetic acid; iv) S-methylisothiourea bis-benzyloxycarbonyl, base, tetrahydrofuran; v) calcium chloride, sodium borohydride in tetrahydrofuran and ethanol; vi) HCl (anhydrous). "*" indicates the position of an asymmetric carbon atom.

1 Compounds of the present invention have the formula:

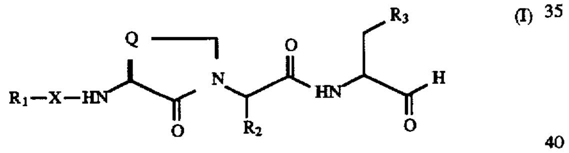

wherein:

(a) X is selected from the group consisting of —S(O)$_2$—, —NH—S(O)$_2$—, N(R')—S(O)$_2$—, —C(=O)—, —OC(=O)—, and —NH—C(=O)— wherein R' is alkyl of 1 to about 4 carbon atoms, aryl of about 6 to about 14 carbon atoms or aralkyl of about 6 to about 15 carbon atoms;

(b) $R_1$ is selected from the group consisting of:

(1) alkyl of about 3 to about 10 carbon atoms, (2) alkyl of 1 to about 3 carbon atoms substituted with cyclic alkyl of about 5 to about 8 carbon atoms, (3) alkenyl of about 3 to about 6 carbon atoms which is optionally substituted with cyclic alkyl of about 5 to about 8 carbon atoms, (4) aryl of about 6 to about 14 carbon atoms which is optionally mono-substituted with $Y_1$ and $Y_2$, (5) aralkyl of about 6 to about 15 carbon atoms which is optionally mono-substituted in the aryl ring with $Y_1$ or optionally di-substituted in the aryl ring with $Y_1$ and $Y_2$, (6) aralkenyl of about 8 to about 15 carbon atoms which is optionally mono-substituted in the aryl ring with $Y_1$ or optionally di-substituted in the aryl ring with $Y_1$ and $Y_2$,

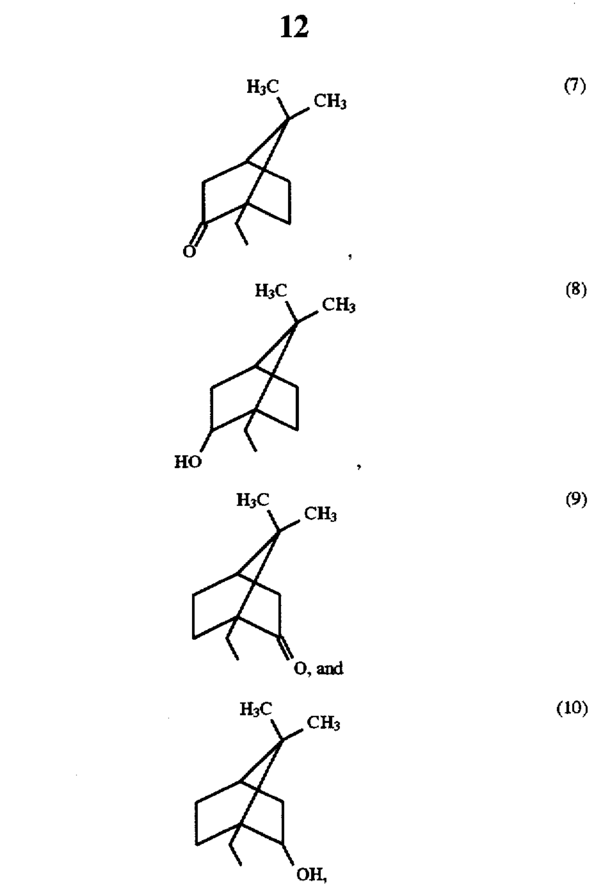

where $Y_1$ and $Y_2$ are independently selected from halogen, cyano, nitro, —COOH, —C(O)OZ$_1$, —Z$_1$, —OZ$_1$, —OH, —P(O)$_3$H, tetrazolyl, —S(O)$_3$H and —S(O)$_m$Z$_1$ wherein m is 0, 1 or 2 and $Z_1$ is alkyl of 1 to about 12 carbon atoms, aryl of about 6 to about 14 carbon atoms and aralkyl of about 6 to about 15 carbon atoms;

(c) Q is selected from the group consisting of —CH$_2$—, —(CH$_2$)$_2$—, and —CH$_2$S(O)$_n$— where n is 0, 1 or 2;

(d) $R_2$ is selected from the group consisting of hydrogen, alkyl of 1 to 4 carbon atoms or alkenyl of 2 to 4 carbon atoms; and (e) $R_3$ is selected from the group consisting

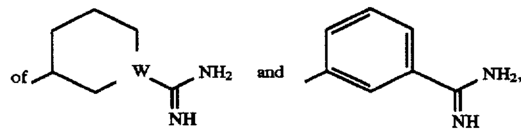

where W is nitrogen or carbon; and pharmaceutically acceptable salts thereof.

Preferred X groups include —SO$_2$—.

Preferred $R_1$ groups include aralkyl and aryl groups. Suitable aryl groups include substituted and unsubstituted phenyl and naphthyl groups. Preferred substitutions for $R_1$ groups include —C(O)OH, —C(O)OZ$_1$, —S(O)$_m$Z$_1$, and —S(O)$_3$H. Especially preferred for $R_1$ are aralkyl groups, more preferred are substituted or unsubstituted benzyl groups. Especially preferred $R_1$ groups on substituted or unsubstituted benzyl groups.

Preferred are compounds where Q is —(CH$_2$)$_2$—.

Preferred are $R_2$ groups include hydrogen.

Preferred $R_3$ groups include those having a saturated six membered ring. Especially preferred are those $R_3$ groups where W is nitrogen.

Accordingly to a preferred aspect, provided are novel compounds wherein X is —$S(O)_2$—, $R_1$ is aralkyl, more preferably substituted or unsubstituted benzyl; Q is —$(CH_2)_2$—, $R_2$ is hydrogen and $R_3$ is a saturated six-membered ring, more preferably a ring wherein W is nitrogen.

According to another aspect, the present invention is directed to salts of the compounds of formula (I). "Salt" includes within its definition, salts of the compounds of the present invention derived from the combination of such compounds and an organic or inorganic acid. In practice, the use of the salt form amounts to use of the base form. The compounds of the present invention are useful in both free base and salt form, with both forms being considered as being within the scope of the present invention. These salts include acid addition salts, for example, salts of hydrochloric acid, hydrobromic acid, acetic acid, benzene sulfonic acid and other suitable acid addition salts.

2. Preparation of Preferred Compounds

Certain intermediates of the present invention are used for the preparation of the compounds of the present invention. For example, 3-[3-piperidyl-(N-guanidino(bis-benzyloxycarbonyl))]-L-alaninol, hydrochloride salt, of Example 5 and (S)-3-[(tert-butoxycarbonyl)amino]-2-oxo-1-piperidineacetic acid of Example 6 are made and coupled to provide certain compounds of the present invention.

FIG. 1 exemplifies a preferred reaction scheme for preparation of one preferred intermediate, 6, used in the preparation of the compounds of the present invention. Examples 1 through 5 provides the details of the preferred scheme. As shown in FIG. 1, 6 is prepared in stepwise fashion beginning with N-(t-butoxycarbonyl)-3-(3-pyridyl)alanine, 1 as described below.

1 is esterified with loss of the Boc group, which is then reintroduced to yield an ester, 2. Preferred methods of esterification employ conditions allowing esterification by use of reagents, such as thionyl chloride with an alcohol or diazomethane. Especially preferred methods of esterification include the use of with thionyl chloride and alcohols Preferred alcohols include methanol ethanol, propanol, isopropanol or butanol. Especially preferred alcohols include methyl alcohol. Preferred reagents for re-introducing of the Boc group on to the N-alpha nitrogen of 1 include di-t-butyldicarbonate.

2 is hydrogenated to convert its aromatic ring to a saturated ring to give 3. Preferred methods of hydrogenation include those using hydrogen gas and a catalyst. Preferred catalysts include platinum oxide, rhodium on aluminum and rhodium on carbon. Especially preferred catalysts include platinum oxide.

3 is treated so as to introduce a protected guanidino group to give 4. Preferred methods of introducing a protected guanidino groups would include the reaction of amino group of 3 with his protected S-methylisothiourea.

4 is reduced to convert its ester group to an alcohol group to give to 5. Preferred methods of reducing ester groups to alcohol groups include the use of reducing agents such as calcium borohydride, lithium borohydride, sodium borohydride, lithium aluminum hydride or sodium metal in ethanol. Especially preferred methods of reduction include the use of calcium borohydride.

5 is treated to convert its Boc-protected amino group to a free N-alpha amino group to give 6. Preferred methods of removing the Boc group include treatment of 5 with HCl in alcohol, trifluoroacetic acid in a chlorinated hydrocarbon solvent, HCl in acetic acid, HCl in ethereal solvents, HCl in ethyl acetate or methyl acetate, p-toluenesulfonic acid in toluene. Especially preferred methods include treatment of 5 with anhydrous HCl in ethyl acetate at 15°–30° C., more preferably at 20°–25° C.

Figure 2:
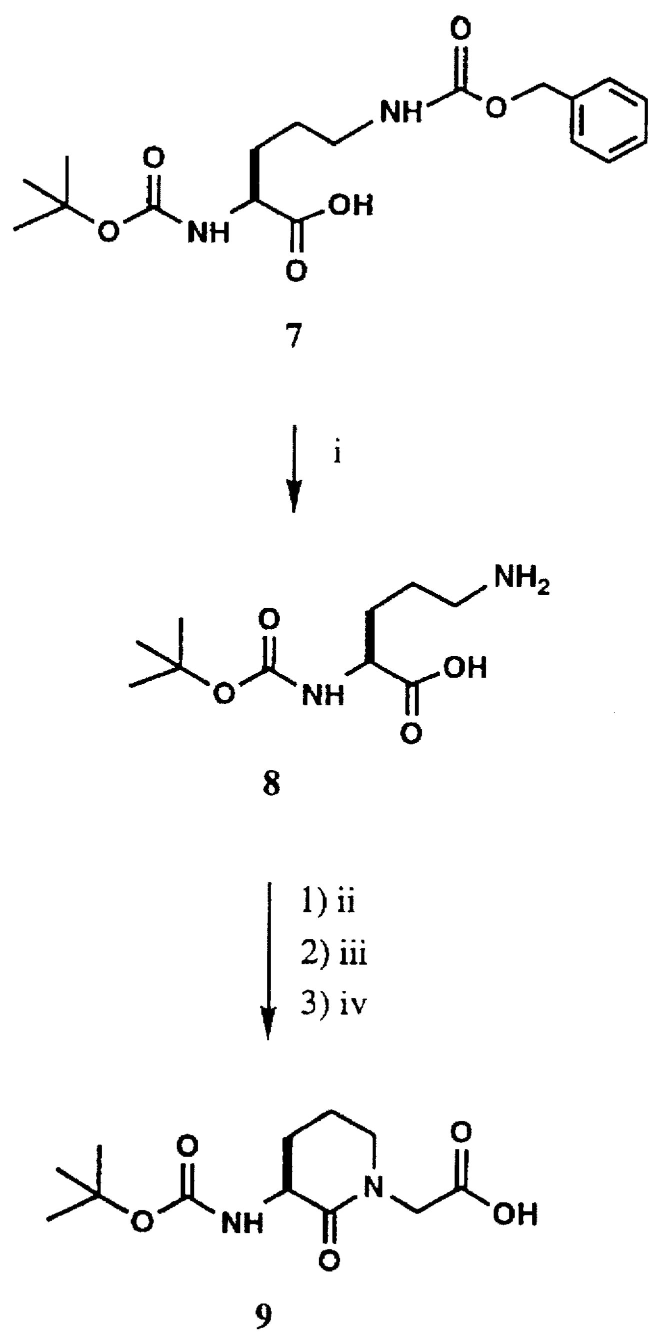
FIG. 2 depicts the reaction scheme for preparation of an intermediate used for the synthesis of the compounds of the present invention. In this figure, "i" through "iv" are defined as: i) hydrogen gas, 10% palladium on carbon; ii) glyoxylic acid; iii) hydrogen gas, 10% palladium on carbon; and iv) 50°–60° C.

FIG. 2 exemplifies a preferred reaction scheme for the preparation of another preferred intermediate 9 used in the preparation of the compounds of the present invention. Example 6 provides the details of the preferred scheme.

As shown in FIG. 2, N-alpha-Boc-N-delta-benzyloxycarbonyl-L-ornithine 7 is hydrogenated with hydrogen gas and palladium on carbon to give 8, which is then reacted with glyoxylic acid, hydrogenated with hydrogen gas and palladium on carbon, and heated at an elevated temperature to give 9.

Figure 3:
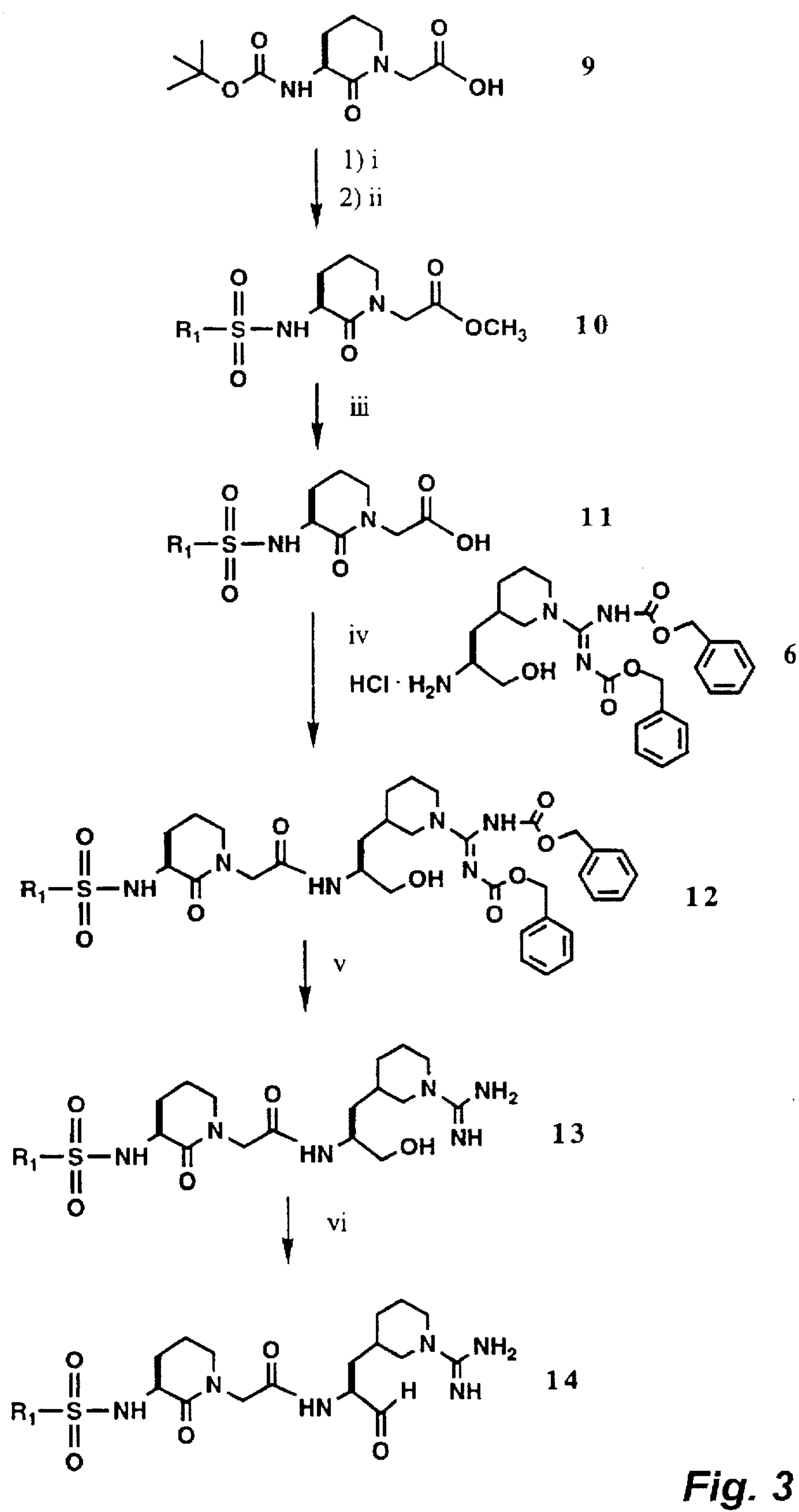
FIG. 3 depicts a preferred reaction scheme for a synthesis of certain compounds of the present invention. In this figure, "i" through "vi" are defined as: i) HCl in methanol; ii) triethylamine, $R_1$-$SO_2Cl$ wherein $R_1$ is as defined herein; iii) 1.0M lithium hydroxide; iv) HOBt, EDC, dimethylaminopyridine, triethylamine; v) hydrogen gas, 10% palladium on carbon; and vi) dimethylsulfoxide, toluene, dichloroacetic acid and EDC.

The compounds of the present invention may be prepared by the preferred reaction schemes depicted in FIG. 3. Examples 7 through 12 provide the details of the preferred scheme.

For example, as shown in FIG. 3, treatment of 9 with saturated HCl in an alcohol removes its Boc group and converts its carboxy group to an ester, which free amino group is then reacted with a sulfonyl chloride, depicted by $R_1$—$S(O)_2$—Cl to give 10. $R_1$ is as defined herein. 10 is base hydrolysed to give 11 which has a free carboxy group. 11 is coupled to 6 (prepared as described in Examples 1 through 5) by carbodiimide coupling to give 12. 12 is hydrogenated with hydrogen gas and palladium on carbon to give 13. 13 is oxidized using dimethylsulfoxide, dichloroacetic acid, toluene and EDC to give 14. 13 may also be oxidized to 14 using pyridine trioxide, triethylamine and dimethylsulfoxide.

The preferred means of chemically coupling (as for example, 11 to 6 of FIG. 3) include formation of a peptide bond by using conventional coupling reagents known in the art. See Bodanszky, N., Peptide Chemistry, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling of the include DCC with HOBt, EDC with HOBt, HBTU, TBTU, HBTU with HOBt, and TBTU with HOBt. In two-step coupling, an activated ester or anhydride of the C-terminal carboxy group of one coupling partner is formed prior to its coupling to the other coupling partner.

3. Selection of Preferred Compound

The compounds of the present invention are screened for their ability to inhibit thrombin, plasmin, tissue plasminogen activator (t-PA), activated protein C (aPC), chymotrypsin, and trypsin as set forth below. Certain of the preferred compounds are distinguished by their ability to inhibit thrombin, while not substantially inhibiting plasmin, t-PA, aPC, chymotrypsin, and trypsin. With respect to thrombin and the other enzymes and as used herein, the term "not substantially inhibiting" means that the $IC_{50}$ (or Ki) for plasmin, t-PA, aPC, chymotrypsin, and trypsin for a given compound is greater than or equal to its $IC_{50}$ (or Ki, respectively) for thrombin.

The compounds of the present invention are dissolved in buffer to give solutions containing concentrations such that assay concentrations range from 0 to 100 micromolar. In the assays for thrombin, plasmin, t-PA, aPC, chymotrypsin, and trypsin, a chromogenic synthetic substrate is added to a solution containing test compound and the enzyme of interest and the residual catalytic activity of that enzyme is determined spectrophotometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rate of substrate turnover caused by the specific enzyme being measured at various enzyme concentrations. $K_i$ is that concentration of test compound giving 50% inhibition of the rate of substrate turnover. Examples A and B provide an exemplar of the in vitro assays used to select the compounds of the present invention.

Certain of the preferred compounds of the present invention have a $K_i$ of about 0.001 to about 200 nM in the thrombin assay. Especially preferred compounds have a $K_i$ of about 0.001 to about 50 nM. The more especially preferred compounds have a Ki of about 0.001 to about 10 nM.

Certain of the preferred compounds of the present invention have a $IC_{50}$ for plasmin, t-PA, aPC, chymotrypsin, and trypsin which is at least 10 times greater than its $IC_{50}$ for thrombin. Especially preferred compounds have an $IC_{50}$ for plasmin, t-PA, aPC, chymotrypsin, and trypsin which is about 20 to about 100,000 times greater than its $IC_{50}$ for thrombin. More especially preferred compounds have an $IC_{50}$ for plasmin, t-PA, aPC, chymotrypsin, and trypsin which is about 100 to about 1,000,000 times greater than its $IC_{50}$ for thrombin. In the event that a compound of the present invention has an $IC_{50}$ with respect to plasmin, t-PA, aPC, chymotrypsin, or trypsin which is greater than the highest concentration of compound tested, the $IC_{50}$ is taken to be that highest concentration of compound.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in *Remington's Pharmeceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixers for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

5. Utility and Method

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vacuum therein as a means to draw blood obtained by venipuncture into the tube is well known in the medical arts. Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of factor Xa or thrombin, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a therapeutically effective amount of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

To assist in understanding, the present invention will now be be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Preparation of N-(t-butoxycarbonyl)-3-(3-pyridyl)-L-alanine methyl ester

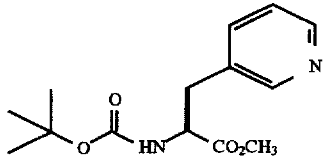

To a solution of N-(t-butoxycarbonyl) -3-(3-pyridyl) alanine (5.0 g, 18.8 mmole) in methanol 100 mL) was added thionyl chloride (2M solution in dichloromethane, 66 mL, 132 mmole) and the solution was stirred overnight at ambient temperature. The methanol was removed under reduced pressure to a minimum volume and ethyl acetate (100 mL) was added. The resulting white precipitate was collected on a glass funnel. To a solution of the collected precipitate in a mixture of tetrahydrofuran/water (40 mL each) was added di-tert-butyl dicarbonate (4.8 g, 21.99 mmole ) and sodium carbonate (1.95 g, 18.4 mmole). After stirring for 12 hours at ambient temperature, the reaction mixture was diluted with ethyl acetate (40 mL) and washed with a solution of saturated sodium bicarbonate (25 mL). The organic layer was dried over anhydrous sodium sulfate and concentrated under vacuum to give crude product. This was subjected to flash column chromatography on silica gel (230–400 mesh) column (8×52 cm), eluting with a 10:90 mixture of ethyl acetate/hexane followed by a 60:40 mixture of ethyl acetate/hexane. 4 g (74%) of the title compound was obtained as an oil. Thin-layer chromatography gave an Rf=0.68 (silica gel; ethyl acetate).

Example 2

Preparation of N-(t-butoxycarbonyl)-3-(3-piperidyl)-L-alanine methyl ester, acetate salt

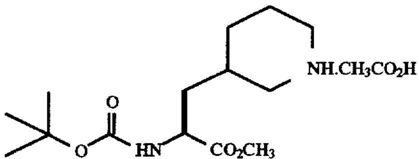

A solution of the compound of Example 1 (5 g, 17.8 mmole) in ethanol (24 mL), acetic acid (6 mL) and water (6 mL) was hydrogenated over platinum oxide (500 mg) at 45 psi for three hours. The catalyst was filtered off and the filtrate concentrated under vacuum to an oily residue (6.89 g) which was taken to the next step without further purification. Thin-layer chromatography in a yielded two spots corresponding to two diastereomers with Rf values of 0.16 and 0.26, respectively (silica gel; 4:1:1 n-butanol/acetic acid/water).

Example 3

Preparation of N-(t-butoxycarbonyl) -3- [3-piperidyl-(N-guanidino (bis-benzyloxycarbonyl))]-L-alanine methyl ester

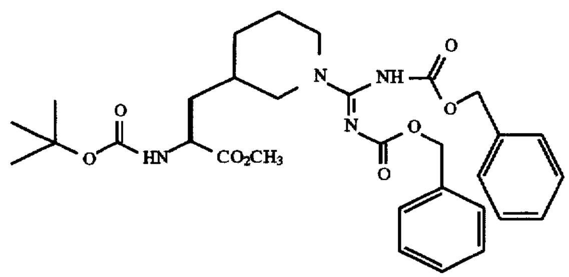

To a solution of the compound of Example 2 (6.89 mm 19.9 mmole) in tetrahydrofuran (80 mL) was added the S-methylisothiourea bis-benzyloxycarbonyl (7.13 g, 19.9 mmole) followed by N-methylmorpholine (4.37 mL), and the reaction was stirred at ambient temperature for 18 hours. The reaction mixture was concentrated under vacuum and the resulting residue was picked-up in ethyl acetate (100 mL) and washed with 1N sodium bisulfate and saturated sodium chloride (50 mL each). After drying over anhydrous sodium sulfate, the solvents were removed under vacuum and the crude title compound was subjected to flash column chromatography on silica gel (230–400 mesh) column (5.5×45 cm) eluting with 1:9 ethyl acetate/hexanes (two column volumes), followed by 1:1 ethyl acetate/hexanes. 2.75 g the title compound was obtained as a mixture of two diastereomers. Thin-layer chromatography gave two spots with $R_f$ values of 0.57 and 0.62, respectively silica gel; 1:1 ethyl acetate/hexanes).

Example 4

Preparation Of N-(t-butoxycarbonyl)-3-[3-piperidyl-(N-guanidino (bis-benzyloxycarbonyl))]-L-alaninol

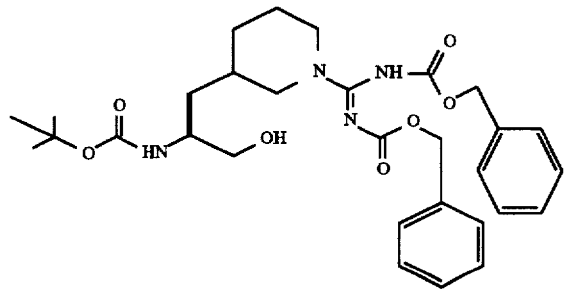

To a stirred solution of the compound of Example 3 (2.23 g, 3.7 mmole) in absolute ethanol (8 mL) and anhydrous tetrahydrofuran (4 mL) was added calcium chloride (844 mg, 7.6 mmole) and sodium borohydride (575 mg, 15.2 mmole). After 12 hours at ambient temperature, the reaction mixture was concentrated under vacuum and the resulting residue was partitioned between ethyl acetate and 1N sodium bisulfate (10 mL each). After separating the two layers, the organic layer was washed twice more with 1N sodium bisulfate, dried over anhydrous sodium sulfate and concentrated under vacuum gave a residue. Flash column chromatography of the residue on silica gel (230–400 mesh) column (8×52 cm) eluting with ethyl acetate affords 1.3 g of the title compound as a white foam. Thin layer chromatography yielded two spots corresponding to two diastereomers with $R_f$ values of 0.18 and 0.27, respectively (silica gel; 1:1 ethyl acetate/hexanes).

Example 5

Preparation of 3-[3-piperidyl-(N-quanidino(bis-benzyloxycarbonyl))]-L-alaninol, hydrochloride salt

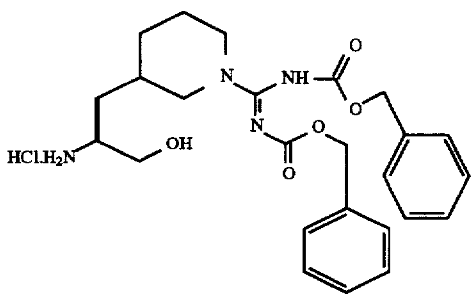

The compound of Example 4 (290 mg, 0.57 mmole) was treated with 2.5N anhydrous hydrochloric acid in ethyl acetate (2.0 mL) at ambient temperature for one hour. The solvent was removed under vacuum to a sticky-white solid (260 mg). This was taken to the next step without further purification. 1H NMR spectrum taken in $CD_3OD$ showed no butoxycarbonyl protons at 1.4 ppm.

Example 6

Preparation of (S)-3-[(tert-butoxycarbonyl)amino]-2-oxo-1-piperidineacetic acid

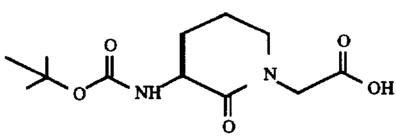

This compound was made in 4 steps by a modification of the literature procedure of D. F. Veber and R. M. Freidinger, U.S. Pat. No. 4,192,875 (Mar. 11, 1980; and R. M. Freidinger, et. al., J. Org. Chem.,47:104–109 (1982). The new method disclosed below proceeds through cleaner intermediates and thus allows for the preparation of large quantities of material in a high state of purity.

N-alpha-Boc-N-delta-benzyloxycarbonyl-L-ornithine (100.3 g, 0.27 mole) was dissolved in a solution of methanol (450 mL), water (320 mL) and acetic acid (46.5 mL). 10% palladium on carbon catalyst (10.0 g) was added and the mixture was hydrogenated on a Parr apparatus at 35 psi for 2.5 hours. Thin-layer chromatography (silica gel; 20:10:3 dichloromethane/methanol/acetic acid; ninhydrin) showed clean conversion to N-alpha-Boc-L-ornithine.

After purging with nitrogen, glyoxylic acid (27.72 g, 0.30 mole) was added, the mixture was stirred at ambient temperature for 50 hours, hydrogenated at 35 psi for 17 hours, and the catalyst was filtered off. A fresh portion of 10% palladium on carbon catalyst (5 g) was added and the mixture was hydrogenated for a further 20 hours on the Parr Shaker at 40 psi. The catalyst was removed by filtration and the filtrate was concentrated to dryness under vacuum. The residue was taken up in methanol and reevaporated. This process was repeated and the residue was pumped at <1 mm fig overnight to afford a yellow foam.

The crude intermediate was dissolved in dry dimethylformamide (625 mL) and heated to 50°–60° C. for 2.5 hours. The solvent was removed under vacuum at 80° C. The resultant oil was dissolved in 500 mL of dichloromethane and extracted with 500 mL of 1M sodium hydroxide solution. The aqueous solution was extracted with 500 mL of dichloromethane, acidified with cooling with 550 mL of 1M HCl, re-extracted with 5×500 mL dichloromethane and 2×500 mL 9:1 dichloromethane/isopropanol. The combined organic layers were dried over anhydrous magnesium sulfate and evaporated to afford 50 g (67% yield) of the title compound as a solidifying oil, judged pure (single spot with Rf=0.30) by thin-layer chromatography (silica gel; 27:3:1 dichloromethane/methanol/acetic acid).

Example 7

Preparation of norVal(cyclo)-Gly-O-methyl ester, hydrochloride salt

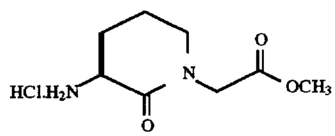

The compound of Example 6 (43.5 g, 0.160 mole) was dissolved in 150 mL of absolute methanol, cooled to 0° C., and treated dropwise with saturated HCl in methanol (400 mL). The solution was stirred at 0° C. for 1 hour and then warmed to ambient temperature and stirred for 14 hours. The solution was concentrated under vacuum to afford the title compound as a clear oil which was used directly in the next example. Thin-layer chromatography gave an Rf=0.25 (silica gel; 27:3:1 dichloromethane/methanol/ concentrated ammonium hydroxide).

Example 8

Preparation of N-benzylsulfonyl-norVal(cyclo)-Gly-O-methyl ester

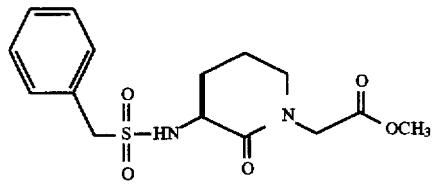

The compound of Example 7 (19.1 g, 85.8 mmole) was slurried in 850 mL of dry acetonitrile and was treated with benzylsulfonyl chloride (32.7 g, 0.172 mole). The solution was cooled to 0° C. and treated dropwise with triethylamine (60.0 mL, 0.428 mole). After 2 hours, an additional portion of benzylsulfonyl chloride (16.4 g, 85.8 mmole) was added. The solution gradually warmed to ambient temperature and was stirred for 16 hours. The solids were filtered and the filtrate was concentrated under vacuum to give an oil. The oil was purified by flash column chromatography (silica gel; eluting with a gradient of 10–50% diethyl ether in dichloromethane) to give 19.8 g (68% yield) of the title compound as a white foam. Thin-layer chromatography gave an Rf=0.55 (silica gel; 27:3:1 dichloromethane/methanol/acetic acid).

Example 9

Preparation of N-benzylsulfonyl-norVal(cyclo)-Gly

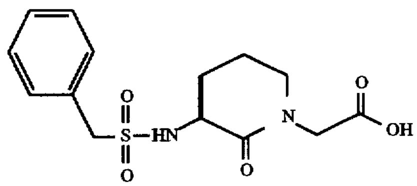

The compound of Example 8 (17.2 g, 52.7 mmole) was dissolved in 350 mL of methanol, cooled to 0° C., and treated with 1.0M lithium hydroxide in water (116 mL) dropwise. After 1 hour, the reaction mixture was allowed to warm to ambient temperature and was stirred for 18 hours. Dowex 50×8-400 ion-exchange resin ($H^+$ form, 49 g) was added to the slurry to adjust the pH to 3. After stirring for 30 minutes, the slurry was filtered and the resin was washed with several portions of water/methanol. The filtrate was concentrated under vacuum. The resulting residue was taken up in acetonitrile and concentrated under vacuum. This was repeated one more time to give 17.2 g (100% yield) of the title compound as a colorless, amorphous solid. Thin-layer chromatography gave an Rf=0.30 (silica gel; 27:3:1 dichloromethane/methanol/acetic acid).

Example 10

Preparation of benzylsulfonyl-norVal(cyclo)-Gly-3-[3-piperidyl -(N-guanidino-bis-benzyloxycarbonyl))]-L-alaninol

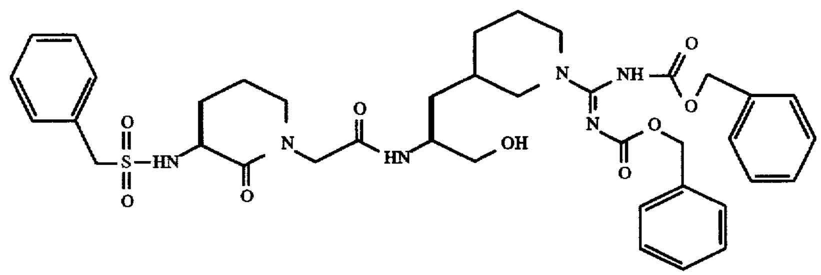

To a suspension of the compound of Example 5 (1.4 g, 2.8 mmole) in acetonitrile (10 mL) was added successively the compound of Example 9 (822 mg, 2.5 mmole), EDC (480 mg, 2.5 mmole), HOBt (402 mg, 2.62 mmole), dimethylaminopyridine (40 mg, 0.33 mmole) and triethylamine (12.5 mmole, 1.74 mL). The solution was stirred at ambient temperature for twelve hours. The solvent was removed under vacuum and the resulting residue was picked up in ethyl acetate (30 mL) and washed two times each with 10 mL portions of 1N sodium bisulfate, saturated sodium bicarbonate and brine. The organic layer was dried over anhydrous sodium sulfate and concentrated under vacuum to give crude product. This was chromatographed on a silica gel (230–400 mesh) column (5×40 cm) eluting with a 95:5 dichloromethane/methanol (two column volumes). 970 mg (78%) the title compound was obtained which consisted of a mixture of two diastereomers. Thin-layer chromatography gave an Rf=0.31 (silica gel; 95:5 dichloromethane/methanol).

Example 11

Preparation of alpha-N-benzylsulfonyl-norVal(Cyclo)-Gly-L-prolyl -3-[3-piperidyl-(N-guanidino)]-L-alaninol, acetate salt

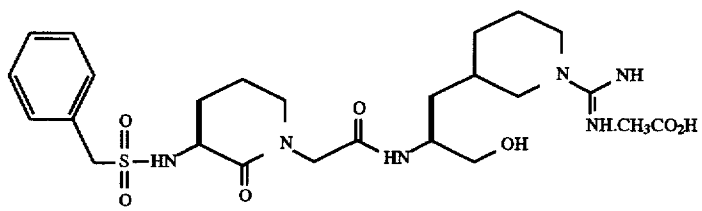

The compound of Example 10 (970 mg, 1.25 mmole) was subjected to catalytic hydrogenation in methanol (50 mL) and acetic acid (5 mL) in the presence of 10% palladium on carbon (90 mg) at 45 psi for 3 hours. The product was obtained as an oil in quantitative yield after removing the solvent under vacuum. Analytical HPLC using a 4.6×250 mm reverse phase column, containing a C-18 resin comprised of 10 micron size gel particles with a 300 angstrom pore size, using a gradient ranging from 10–25% acetonitrile in water (containing 0.1% trifluoroacetic acid) showed two peaks of equal intensity with retention times of 15 minutes at 16.5 minutes respectively. Fast atom bombardment mass spectrometry confirmed the theoretical molecular weight of 508.

Example 12

Preparation of benzylsulfonyl-norVal(cyclo)-Gly-L-prolyl-3-[3-piperidyl-(N-guanidino)]-L-alaninal

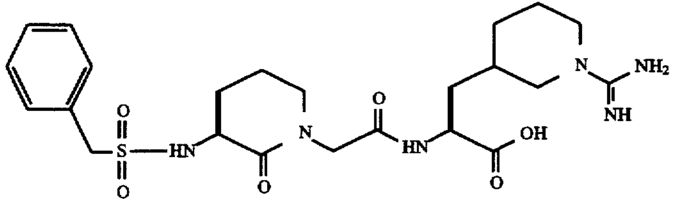

To a chilled solution of the compound of Example 11 (730 mg, 1.3 mmole) in dimethylsulfoxide and toluene (20 mL each) was added dichloroacetic acid (0.59 mL, 7.1 mmole) followed by EDC (2.75 g, 14.3 mmole) at one minute later. The reaction was stirred for 5 minutes at 0° C. and for 85 minutes at ambient temperature, and then was quenched with 50 mL water. The water layer was extracted twice with diethyl ether (15 mL portions), diluted to 100 mL of water and subjected to HPLC using a 47×300 mm reverse phase column, containing a C-18 resin comprised of 10 micron-size gel particles with a 300 angstrom pore size, eluting with a gradient ranging from 10–20% acetonitrile in water (containing 0.1% trifluoroacetic acid). The two diastereomers obtained had retention times of 16 (referred to as isomer "26A" ) and 18 minutes (referred to as isomer "26B" ) respectively. 180 mg of the faster-moving diastereomer, 229 mg of the slower-moving diastereomer and 95 mg of a mixture of the two diastereomers of the title compounds were recovered. Fast atom bombardment mass spectrometry confirmed the theoretical molecular weight of 506 for both diastereomers.

Example A

Kinetic Analysis of $BzlSO_2$-norVal(cyclo)-Gly-Ala(3-guanPip)-al (Isomer B) in an in vitro Thrombin Inhibition Assay The ability of the compound of Example 12, $BzlSO_2$-norVal (cyclo)-Gly-Ala(3-guanPip)-al, isomer 26B, hereinafter referred to Isomer B, of the present invention to act as an inhibitor of thrombin catalytic activity was assessed by determining the inhibition constant, Ki.

Enzyme activity was determined using the chromogenic substrate Pefachrome t-PA ($CH_3SO_2$-D-hexahydrotyrosine-glycyl-L-Arginine-p-nitroanilide), obtained from Pentapharm Ltd. The substrate was reconstituted in deionized water prior to use. Purified human alpha-thrombin (3000U/mg specific activity) was obtained from Enzyme Research Laboratories, Inc. The buffer used for all assays was HBSA (10 mM HEPES, pH 7.5, 150 mM sodium chloride, 0.1%, bovine serum albumin).

The assay for the Ki determination was conducted by combining in appropriate wells of a Corning microtiter plate, 50 microliters of HBSA, 50 microliters of Isomer B at a specified concentration diluted in HBSA (or HBSA alone for $V_{o\ (uninhibited\ velocity)}$ measurement), and 50 microliters of the chromogenic substrate (250 micromolar, 5-times Km) At time zero, 50 microliters of alpha-thrombin diluted in HBSA, was added to the wells yielding a final concentration of 0.5 nM in a total volume of 200 microliters. Velocities of chromogenic substrate hydrolysis which occurred over 40 min was measured by the change in absorbance at 405 nm using a Thermo Max® Kinetic Microplate Reader. The Ki value for isomer B was determined using the relationships developed by Williams and Morrison, Methods in Enzymology, 63: 437 (1979) using steady state velocities (Vs) measured over 40 minutes. The extent of substrate hydrolysis was less than 5% over the course of this assay. Table 1 below gives the Ki values for Isomer B described in this patent. The data shows the utility of this compound as a potent in vitro inhibitor of human alpha-thrombin.

TABLE 1

Inhibitor Constant (Ki) of Bz1$SO_2$-norVal (cyclo)-Gly-Ala (3-guanPip)-al (Isomer B) against human alpha-thrombin amidolytic activity.

| Compound | Ki (nM)* |
|---|---|
| Isomer B | 0.318 ± 16 |

*Mean ± SD, n = 3

Example B

In vitro Enzyme Assays for Specificity Determination

The ability of Isomer B (Bzl$SO_2$-norVal(cyclo)-Gly-Ala (3-guanPip)-al) of the present invention to act as a selective inhibitor of thrombin catalytic activity was assessed by determining the concentration of this compound which inhibited the activity of this enzyme by 50%, ($IC_{50}$), and comparing this value to that determined for the following related serine proteases: recombinant tissue plasminogen activator (rt-PA), plasmin, activated protein C, chymotrypsin, and trypsin.

The buffer used for all assays was HBSA (10 mM HEPES, pH 7.5, 150 mM sodium chloride, 0.1% bovine serum albumin). The assay for $IC_{50}$ determinations was conducted by combining in appropriate wells of a Corning microtiter plate, 50 microliters of HBSA, 50 microliters of Isomer B at a specified concentration (covering a broad concentration range) diluted in HBSA (or HBSA alone for $V_O$ (uninhibited velocity) measurement), and 50 microliters of the enzyme diluted in HBSA. Following a 30-minute incubation at ambient temperature, 50 microliters of the substrate at the concentrations specified below, was added to the wells yielding a final total volume of 200 microliters. The initial velocity of chromogenic substrate hydrolysis was measured by the change in absorbance at 405nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value for Isomer B.

Thrombin Assay

Thrombin catalytic activity was determined using the chromogenic substrate Pefachrome t-PA ($CH_3SO_2$-D-hexahydrotyrosine-glycyl-L-arginine-p-nitroanilide, obtained from Pentapharm Ltd.). The substrate was made up in deionized water followed by dilution in HBSA prior to the assay in which the final concentration was 300 micromolar (about 5-times Km). Purified human alpha-thrombin was obtained from Enzyme Research Laboratories, Inc. The enzyme was diluted into HBSA prior to the assay in which the final concentration was 0.25 nM.

Recombinant tissue plasminogen activator (rt-PA)

rt-PA catalytic activity was determined using the substrate, Pefachrome t-PA ($CH_3SO_2$-D-hexahydrotyrosine-glycyl-L-arginine-p-nitroanilide, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2251 [D-valyl-L-leucyl-L-lysine-p-nitroanilide], which was obtained from Kabi Diagnostica. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC)

aPC catalytic activity was determined using the chromogenic substrate, Pefachrome PC (delta-carbobenzloxy-D-lysine-L-prolyl-L-arginine-p-nitroanilide), obtained from Pentapharm Ltd.). The substrate was made up in deionized water followed by dilution in HBSA prior to the assay in which the final concentration was 250 micromolar (about 3-times Km). Purified human aPC was obtained from Hematologic Technologies, Inc. The enzyme was diluted into HBSA prior to assay in which the final concentration was 1.0 nM.

Chymotrypsin

Chymotrypsin catalytic activity was determined using the chromogenic substrate, S-2586 (methoxy-succinyl-L-arginine-L-prolyl-L-tyrosyl-p-nitroanilide), which was obtained from Kabi Diagnostica. The substrate was made up in deionized water followed by dilution in HBSA prior to the assay in which the final concentration was 100 micromolar (about 9-times Km). Purified (3×-crystallized;CDI) bovine pancreatic alpha-chymotrypsin was obtained from Worthington Biochemical Corp. The enzyme was reconstituted in deionized water and diluted into HBSA prior to assay in which the final concentration was 1.0 nM.

Trypsin

Trypsin catalytic activity was determined using the chromogenic substrate, S-2222 (benzoyl-L-isoleucine-L-glutamic acid-(gamma-methyl ester)-Larginine-p-nitroanilide), which was obtained from Kabi Diagnostica. The substrate was made up in deionized water followed by dilution in HBSA prior to the assay in which the final concentration was 250 micromolar (about 4-times Km). Purified (3×-crystallized; TRL3) bovine pancreatic trypsin was obtained from Worthington Biochemical Corp. The enzyme was reconstituted in deionized water and diluted into HBSA prior to assay in which the final concentration was 0.5 nM.

Table 2 lists the determined $IC_{50}$ values for Isomer B against the enzymes listed above and demonstrates the high degree of specificity of this compound for the inhibition of a-thrombin compared to these related serine proteases.

TABLE 2

$IC_{50}$ value for the inhibition of thrombin amidolytic activity compared to selected serine proteases for Isomer B.

| Enzyme | $IC_{50}$ (nM) Isomer B |
|---|---|
| alpha-thrombin | 0.9 |
| rt-PA | NI** |

TABLE 2-continued

IC$_{50}$ value for the inhibition of thrombin amidolytic activity compared to selected serine proteases for Isomer B.

| Enzyme | IC$_{50}$ (nM) Isomer B |
|---|---|
| Plasmin | NI** |
| aPC | NI** |
| Chymotrypsin | NI** |
| Trypsin | NI** |

**No inhibition observed at the maximal concentration of inhibitor assayed-25,000nM. The data represents the mean of at least two independent experiments.

Example C

Figure 4:
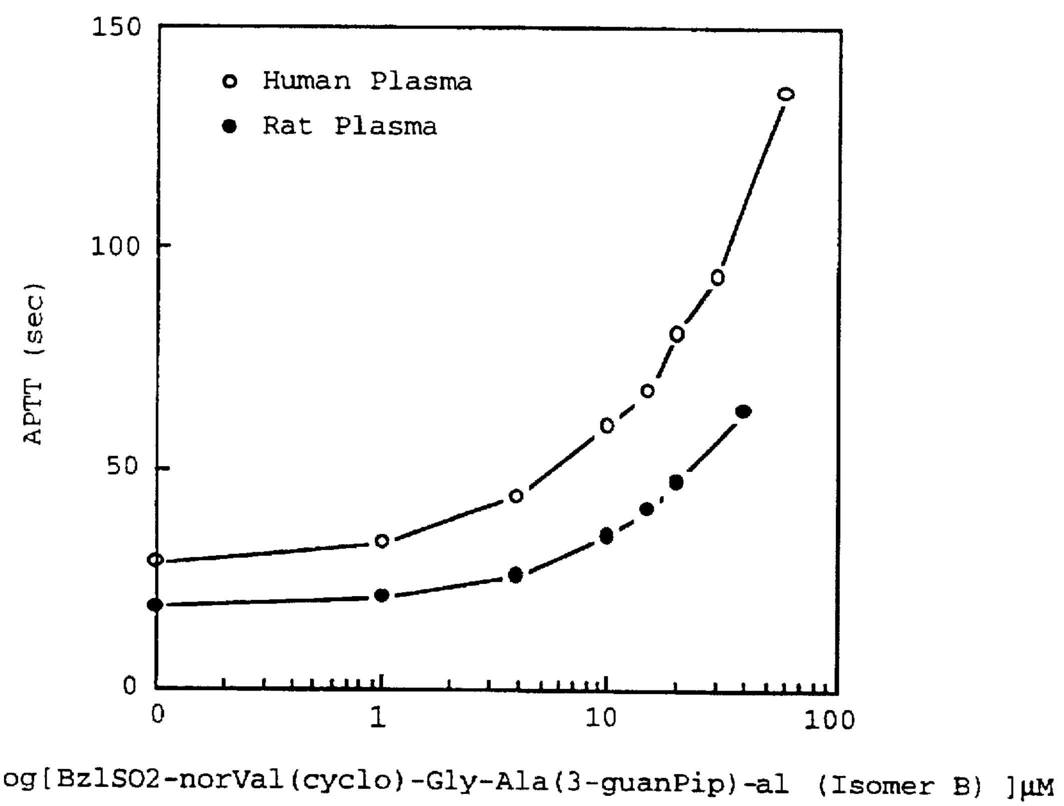
FIG. 4 depicts the anticoagulant effect of $BzlSO_2$-norVal (cyclo) -Gly-Ala(3-guanPip)-al (Isomer 26B) measured in citrated rat (●) and human (○) plasma using the activated partial thromboplastin time (APTT) assay. The control clotting times (0 inhibitor) for rat and human plasma were 19 seconds and 29 seconds, respectively. The concentration of $BzlSO_2$-norVal(cyclo)-Gly-Ala(3-guanPip)al which caused a doubling of the control clotting time in rat and human plasma was 12.7 micromolar and 9.1 micromolar, respectively. The data is the mean of two independent determinations.

Ex vivo Anticoagulant Effects of BzlSO$_2$-norVal(cyclo)-Gly-Ala (3-guanPip)-al (Isomer B) in Rat and Human Plasma The ex vivo anticoagulant effects of Isomer B (BzlSO$_2$-norVal (cyclo)-Gly-Ala (3-guanPip) -al) was determined by measuring the prolongation of the activated partial thromboplastin time (APTT) over a broad concentration range of the added inhibitor, using pooled normal human and rat plasma. Fresh frozen citrated pooled normal human plasma was obtained from George King Biomedical, Overland Park, Kans. Pooled normal rat plasma was prepared from citrated whole blood collected from anesthetized rats using standard procedures. The plasma was flash frozen and stored at −80° C. until use. Measurements APTT was made using the Coag-A-Mate RA4 automated coagulometer (General Diagnostics, Organon Technica, Oklahoma City, Okla.) using the Automated APTT reagent (Organon Technica, Durham, N.C.) as the initiator of clotting according to the manufacturers instructions. The assay was conducted by making a series of dilution's of Isomer B in rapidly thawed plasma followed by adding 200 microliters to the wells of the assay carousel. As shown in FIG. 4, Isomer B prolonged the APTT in a dose dependent manner in both rat and human plasma demonstrating an anticoagulant effect in both species of mammals.

Example D

Evaluation of the Antithrombotic Potential of BzlSO$_2$-norVal (cyclo)-Gly-Ala(3-guanPip)-al (Isomer B) in an Experimental Rat Model of Thrombosis The demonstrated anticoagulant effects of Isomer B (BzlSO$_2$-norVal(cyclo)-Gly-Ala(3-guanPip)-al) in both rat and human citrated plasma indicated that this compound may have potent antithrombotic effects in vive. To investigate this, the antithrombotic (prevention of thrombus formation) properties of Isomer B was evaluated using the following established experimental model of acute vascular thrombosis.

Rat model of FeCl$_3$-induced platelet-dependent arterial thrombosis

This is a well characterized model of platelet dependent, arterial thrombosis which has been used in the evaluation potential antithrombotic compounds such as direct thrombin inhibitors. Kurz, K. D., Main, B. W., and Sandusky, G. E., Thromb. Res., 60: 269–280 (1990). In this model a platelet-rich, occlusive thrombus is formed in a segment of the rat carotid artery treated locally with a fresh solution of FeCl$_3$ absorbed to a piece of filter paper. The FeCl$_3$ is thought to diffuse into the treated segment of artery and causes de-endothelialization of the affected vessel surface. This results in the exposure of blood to subendothelial structures which in turn causes platelet adherence, thrombin formation and platelet aggregation resulting in occlusive thrombus formation. The effect of a test compound on the incidence of occlusive thrombus formation following the application of the FeCl$_3$ is monitored by ultrasonic flowtometry and is used as the primary end point. The use of flowtometry to measure carotid artery blood flow, is a modification of the original procedure in which thermal detection of clot formation was employed. Kurz, K. D., Main, B. W., and Sandusky, G. E., Thromb. Res., 60: 269–280 (1990).

Male Harlan Sprague Dawley rats (420–450 g) were acclimated at least 72 hours prior to use and fasted for 12 hours prior to surgery with free access to water. The animals were prepared, anesthetized with Nembutal followed by the insertion of catheters for blood pressure monitoring, drug and anesthesia delivery. The left carotid artery was isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline) or treatment group with test compound (Isomer B) with at least 6 animals per group per dose. The test compound was administered as a single intravenous bolus at the doses outlined in Table 3 after placement of the flow probe and 5 minutes prior to the thrombogenic stimulus. At t=0, a 3 mm diameter piece of filter paper (Whatman #3) soaked with 10 microliters of a 35% solution of fresh FeCl$_3$ (made up in water) was applied the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point and as a measure of the antithrombotic efficacy of Isomer B.

The antithrombotic efficacy of the Isomer B as an antithrombotic agent in preventing thrombus formation in this in vivo model was demonstrated by the reduction in the incidence of thrombotic occlusion as shown in Table 3 below.

TABLE 3

Evaluation of Isomer B in the FeCl$_3$ Model of Thrombosis in Rats.

| Treatment Group | Dose (mg/kg) | n | Incidence of Occlusion |
|---|---|---|---|
| Saline | — | 6 | 6/6 |
| Isomer B | 0.3 | 6 | 6/6 |
| Isomer B | 1.0 | 6 | 4/6 |
| Isomer B | 3.0 | 6 | 0/6* |

*$p \leqq 0.05$ from saline control by Fishers test

The effective dose which prevents 50% of thrombotic occlusions in this model (ED$_{50}$) can be determined from the above data by plotting the incidence of occlusion versus the dose administered. This allows a direct comparison of the antithrombotic efficacy of Isomer B with other clinically effective antithrombotic agents which have also been evaluated in this model as described above. Table 4 lists the $ED_{50}$ values for several well known anticoagulant agents in this model compared to Isomer B.

TABLE 4

Efficacy of Isomer B compared to other antithrombotic agents based on $ED_{50}$ for thrombus prevention in the $FeCl_3$ model of arterial thrombosis.

| Compound | Ki[a] (nM) | $ED_{50}$[b] (mg/kg) |
|---|---|---|
| Standard Heparin | | 300U/kg |
| Argatroban | 19.0[c] | 3.8mg/kg |
| Hirulog ™ | 2.56[d] | 3.0mg/kg |
| Isomer B | 0.318 | 1.4mg/kg |

[a]Ki determined using human alpha-thrombin as described above and in items c and d.

[b]$ED_{50}$ is defined as the dose that prevents the incidence of complete thrombotic occlusion in 50% of animals tested

[c]Kikumoto, R. et. al., Biochemistry, 23: 85–90 (1984)

[d]Witting, J.I. et. al., Biochem. J., 283: 737–743 (1992)

The data presented in Table 4 clearly demonstrates the effectiveness of Isomer B ($BzlSO_2$-norVal(cyclo)-Gly-Ala Ala(3-guanPip)-al) in preventing occlusive thrombus formation in this experimental model. The relevance of this data to preventing human thrombosis can be inferred from the comparison to the other anticoagulant agents listed in this table which have been evaluated in an identical manner in this experimental model and have demonstrated antithrombotic efficacy in preventing thrombus formation clinically as described in the following literature citations: Heparin: Hirsh, J. N., Engl. J. Mad., 324: 1565–1574 1992, Cairns, J. A. et. al., Chest, 102: 456S–481S (1992); Argatroban: Gold, H. K. et. al., J. Am. Coll. Cardiol., 21: 1039–1047 (1993); and Hirulog™: Sharma, G. V. R. K. et. al., Am. J. Cardiol., 72: 1357–1360 (1993) and Lidón, R. M. et. al., Circulation, 88: 1495–1501 (1993). The in vivo comparison of Isomer B with the clinically effective antithrombotic agents Standard Heparin, Argatroban, and Hirulog™ in the same rodent model of experimental thrombosis coupled with the demonstrated anticoagulant effects of Isomer B in both rat and human plasma described above in Example C would lead one skilled in the art to conclude that this compound will be an effective antithrombotic agent in humans.

We claim:

1. A compound of the formula:

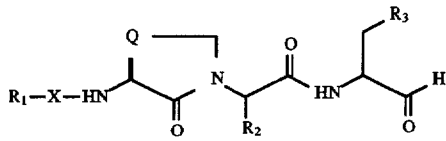

wherein:

(a) X is selected from the group consisting of —S(O)$_2$—, —NH—S(O)$_2$—, N(R')—S(O)$_2$—, —C(=O)—, —OC(=O)—, and —NH—C(=O)— wherein R'is alkyl of 1 to about 4 carbon atoms, aryl of about 6 to about 14 carbon atoms or aralkyl of about 6 to about 15 carbon atoms;

(b) $R_1$ is selected from the group consisting of:

(1) alkyl of about 3 to about 10 carbon atoms, (2) alkyl of 1 to about 3 carbon atoms substituted with cyclic alkyl of about 5 to about 8 carbon atoms, (3) alkenyl of about 3 to about 6 carbon atoms which is optionally substituted with cyclic alkyl of about 5 to about 8 carbon atoms, (4) aryl of about 6 to about 14 carbon atoms which is optionally mono-substituted with $Y_1$ and $Y_2$, (5) aralkyl of about 6 to about 15 carbon atoms which is optionally mono-substituted in the aryl ring with $Y_1$ or optionally di-substituted in the aryl ring with $Y_1$ and $Y_2$, (6) aralkenyl of about 8 to about 15 carbon atoms which is optionally mono-substituted in the aryl ring with $Y_1$ or optionally di-substituted in the aryl ring with $Y_1$ and $Y_2$, (7)

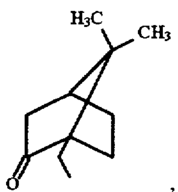

(8)

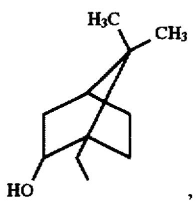

(9)

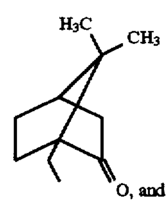

(10)

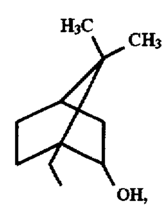

where $Y_1$ and $Y_2$ are independently selected from halogen, cyano, nitro, —COOH, —C(O)OZ$_1$, —Z$_1$, —OZ$_1$, —OH, —P(O)$_3$, tetrazolyl, —S(O)$_3$H and —S(O)$_m$Z$_1$ wherein m is 0, 1 or 2 and $Z_1$ is alkyl of 1 to about 12 carbon atoms, aryl of about 6 to about 14 carbon atoms and aralkyl of about 6 to about 15 carbon atoms;

(c) Q is selected from the group consisting of —CH$_2$—, —(CH$_2$)$_2$—, and —CH$_2$S(O)$_n$— where n is 0, 1 or 2;

(d) $R_2$ is selected from the group consisting of hydrogen, alkyl of 1 to 4 carbon atoms or alkenyl of 2 to 4 carbon atoms; and (e) $R_3$ is selected from the group consisting

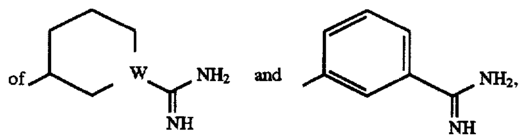

where W is nitrogen or carbon; and pharmaceutically acceptable salts thereof.

2. A compound according to claim 1 wherein X is —S(O)$_2$—.

3. A compound according to claim 2 wherein Q is —CH$_2$—.

4. A compound according to claim 2 wherein Q is —CH$_2$S(O)$_n$—.

5. A compound according to claim 2 wherein Q is —(CH$_2$)$_2$—.

6. A compound according to claim 5 wherein $R_1$ is aryl or aralkyl.

7. A compound according to claim 6 wherein $R_2$ is hydrogen.

8. A compound according to claim 7 wherein $Y_1$ and $Y_2$ are independently selected from —C(O)OH, —C(O)OZ$_1$, —S(O)$_m$Z, and —S(O)$_3$H.

9. A compound according to claim 8 wherein $R_3$ is

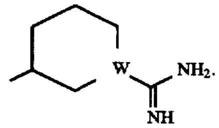

10. A compound according to claim 9 wherein W is nitrogen.

11. A compound according to claim 10 wherein $R_1$ is unsubstituted naphthyl, substituted naphthyl, unsubstituted benzyl or substituted benzyl.

12. A compound according to claim 11 wherein $R_1$ is benzyl.

13. A compound according to claim 1 wherein $R_2$ is hydrogen.

14. A compound according to claim 13 wherein X is —S(O)$_2$.

15. A compound according to claim 14 wherein $R_1$ is aryl or aralkyl.

16. A compound according to claim 15 wherein $R_3$ is

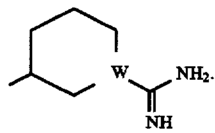

17. A compound according to claim 16 wherein W is nitrogen.

18. A compound according to claim 17 wherein Q is —(CH$_2$)$_2$—or —CH$_2$S(O)$_n$— wherein n is O.

19. A compound according to claim 1 wherein Q is $-(CH_2)_2-$.

20. A compound according to claim 1 wherein X is $-S(O)_2-$, $R_1$ is aralkyl and $R_2$ is hydrogen.

21. A compound according to claim 20 wherein $R_3$ is

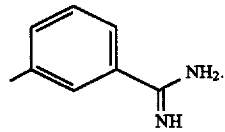

22. A compound according to claim 20 wherein $R_3$ is

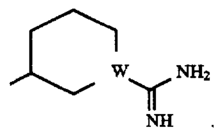

23. A compound according to claim 22 wherein W is nitrogen.

24. A compound according to claim 23 wherein $R_1$ is unsubstituted benzyl or substituted benzyl.

25. A compound according to claim 24 wherein $Y_1$ and $Y_2$ are independently selected from $-C(O)OH$, $-C(O)OZ_1$, $-S(O)_mZ$, and $-S(O)_3H$.

26. A compound according to claim 25 wherein Q is $-(CH_2)_2-$.

27. A compound according to claim 24 wherein Q is $-(CH_2)_2-$.

28. A compound according to claim 23 wherein Q is $-(CH_2)_2-$.

29. A compound according to claim 1 wherein $R_3$ is

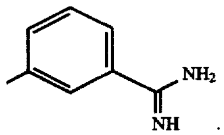

30. A compound according to claim 1 wherein $R_3$ is

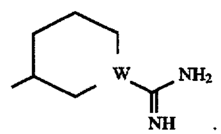

31. A compound according to claim 30 wherein W is nitrogen.

32. A compound according to claim 30 wherein W is carbon.

* * * * *